United States Patent
Flesher et al.

[11] Patent Number: 5,592,283
[45] Date of Patent: Jan. 7, 1997

[54] TESTING OF CONCRETE BY LASER ABLATION

[75] Inventors: Dann J. Flesher, Benton City; David L. Becker, Kennewick; William L. Beem, Kennewick; Tommy C. Berry, Kennewick; N. Scott Cannon, Kennewick, all of Wash.

[73] Assignee: Westinghouse Hanford Company, Richland, Wash.

[21] Appl. No.: 415,842

[22] Filed: Apr. 3, 1995

[51] Int. Cl.⁶ ............................. G01N 3/00; G01N 21/63
[52] U.S. Cl. ................................. 356/72; 356/318; 73/803
[58] Field of Search ........................... 356/72, 317, 318; 73/19.08, 54.03, 803

[56] References Cited

U.S. PATENT DOCUMENTS

| | | |
|---|---|---|
| 3,541,845 | 11/1970 | Kierkegaard-Hansen . |
| 3,700,850 | 10/1972 | Lumley et al. . |
| 3,861,201 | 1/1975 | Kaindl . |
| 4,168,620 | 9/1979 | Schrader ............................... 73/803 |
| 4,480,480 | 11/1984 | Scott et al. . |
| 4,568,814 | 2/1986 | Hamasaki et al. . |
| 4,748,855 | 6/1988 | Barnoff . |
| 4,943,930 | 7/1990 | Radjy . |
| 5,041,987 | 8/1991 | Kuwahara et al. . |
| 5,082,371 | 1/1992 | Ansari . |
| 5,262,967 | 11/1993 | Jaber et al. ............................. 356/378 |

Primary Examiner—F. L. Evans

[57] ABSTRACT

A method of testing concrete in a structure in situ, by: directing a succession of pulses of laser radiation at a point on the structure so that each pulse effects removal of a quantity of concrete and transfers energy to the concrete; detecting a characteristic of energy which has been transferred to the concrete; determining, separately from the detecting step, the total quantity of concrete removed by the succession of pulses; and calculating a property of the concrete on the basis of the detected energy characteristic and the determined total quantity of concrete removed.

13 Claims, 1 Drawing Sheet

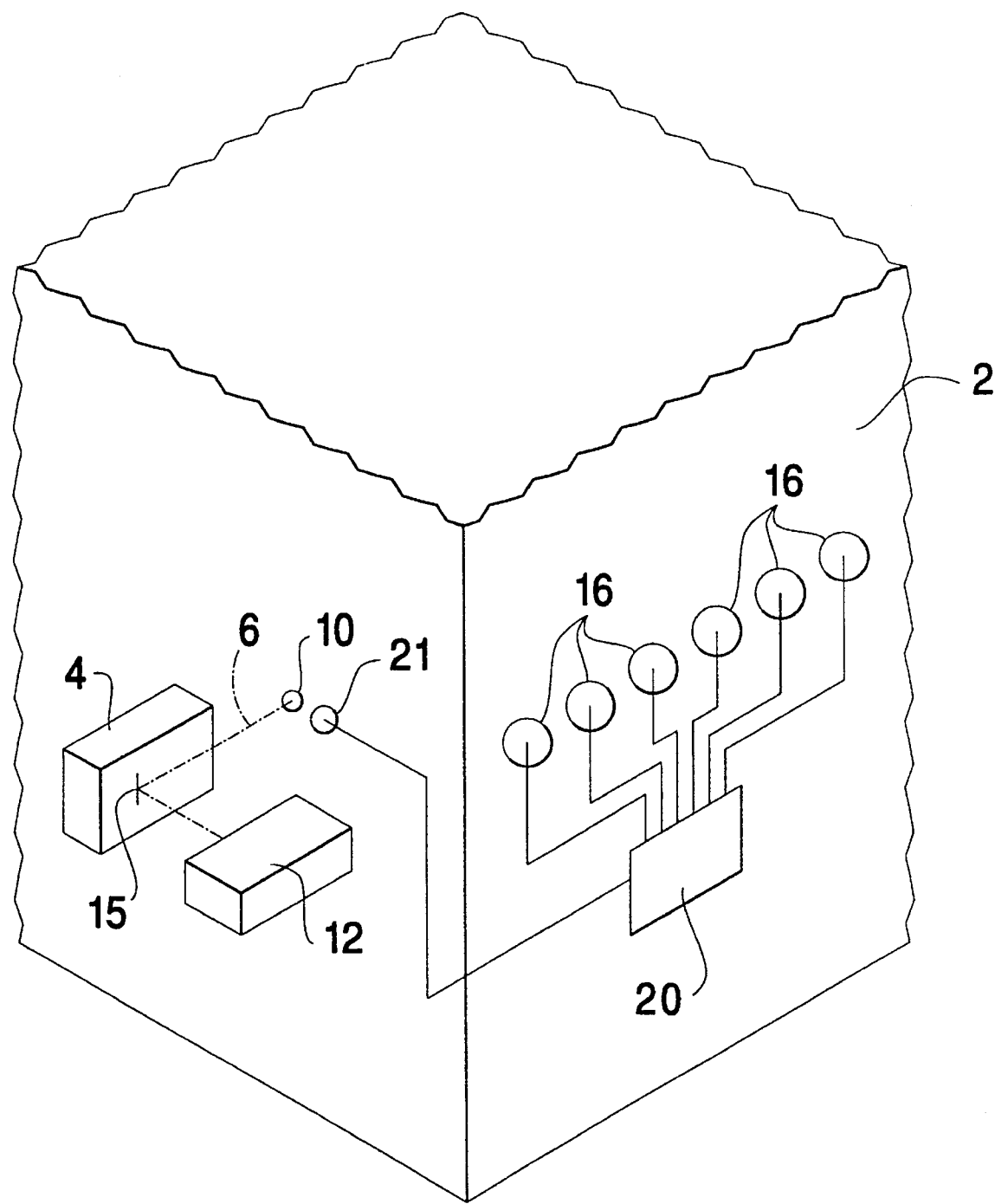

TESTING OF CONCRETE BY LASER ABLATION

ORIGIN OF THE INVENTION

This invention was conceived or first reduced to practice in the course of, or under Contract Number DE-ACO6-87RL10930 between the Westinghouse Hanford Company and the United States Government, represented by the Department of Energy. The United States Government may have rights in this invention.

BACKGROUND OF THE INVENTION

The present invention relates to testing of concrete in fabricated structures or components thereof, and particularly nondestructive testing thereof.

It is frequently desirable to be able to test concrete structures, or sections of such structures, in order to determine whether they have the requisite strength and structural integrity. Heretofore, testing of concrete strength has involved destructive procedures which can not be applied directly to structures that are to continue in use.

In addition, it is known that concrete will experience deterioration over the course of time, which deterioration can be accelerated if the initial concrete composition deviated from that desired, and/or if the concrete was poured under less than optimum atmospheric conditions, and/or if the concrete was subjected to extreme weather fluctuations and/or earth tremors, etc. In the case of concrete structure which are reinforced by steel bars or rods, the reinforcing bars can experience substantial deterioration, particularly if the concrete develops cracks which allow water and air to come in contact with the bars. Presently, there is no convenient procedure for monitoring the physical state of a concrete structure periodically in a nondestructive manner.

U.S. Pat. No. 3,700,850 (Lumley et al) describes removal of material from a workpiece by laser pulse impacts. Each laser impact generates an acoustic shock wave which is propagated through the workpiece. The time of passage of a shock wave from the point of radiation impact to a sensor is indicative of the amount of material removed. When the time of passage has a predetermined value, it is concluded that a predetermined amount of material has been removed from the workpiece. This patent does not identify suitable workpiece materials, but those skilled in the art would understand that machining, the term employed in the patent, is generally performed on metal or plastic workpieces.

SUMMARY OF THE INVENTION

It is an object of the present invention to determine various aspects of the condition of concrete structures.

A specific object of the invention is to determine the strength of concrete structures in situ based on laser pulse impacts.

Another specific object of the invention is to determine, in situ, the structural integrity of, and effects of aging on, concrete structures based on laser pulse impacts.

A further object of the invention is to measure various responses of a concrete structure to laser radiation pulses in order to determine the strength and/or the physical condition of the concrete.

Another specific object of the invention is to determine the chemical composition of the concrete at the points of impact of multiple laser pulses and thereby determine or verify the cement mix, aggregate type, and aggregate distribution.

The above and other objects are achieved, according to the invention, by a method of testing concrete in a structure in situ, comprising: directing a succession of pulses of laser radiation at a point on the structure so that each pulse effects removal of a quantity of concrete and transfers energy to the concrete; detecting a characteristic of energy which has been transferred to the concrete; determining, separately from the detecting step, the total quantity of concrete removed by the succession of pulses; and calculating a property of the concrete on the basis of the detected energy characteristic and the determined total quantity of concrete removed.

BRIEF DESCRIPTION OF THE DRAWING

The sole Figure is a perspective view of a concrete structure and apparatus for testing the structure in accordance with the present invention.

DESCRIPTION OF THE PREFERRED EMBODIMENTS

The present invention is based on an understanding that a beam of laser radiation can be given parameters which allow the beam to remove material from a concrete body and vaporize at least a portion of the removed material while simultaneously generating acoustic shock waves that propagate through the structure. According to the invention, the laser radiation beam is preferably composed of a succession of pulses, the material vaporized by each pulse is spectrum analyzed and/or the acoustic wave generated by each radiation pulse is detected, and the spectrum analysis and/or acoustic wave detection result are correlated with a separate measurement of the total volume of concrete removed by the beam to provide identification of the concrete strength, and/or chemical composition and/or physical state. Such determinations require the removal of only small quantities of concrete.

The Figure shows a portion of a concrete structure 2 which may be tested in accordance with the present invention. The apparatus employed for testing includes a source of laser radiation having an output member 4 which is mounted to direct a beam of laser radiation along a fixed axis 6 at a selected point on concrete structure 2. Laser radiation, preferably in the form of pulses, is emitted along axis 6 in order to vaporize concrete and create a hole, or cavity, 10.

The apparatus further includes a spectral analysis unit 12 having an input port (not visible in the figure) disposed for receiving, via a semireflecting mirror or beam splitter 15, radiation which is emitted by minute samples of the concrete at the point of laser beam contact as a result of being vaporized by the laser radiation.

In addition, along a side surface of structure 2, preferably one which is perpendicular to the surface in which hole 10 is formed, there may be disposed an array of acoustic sensors 16 which will receive acoustic waves produced in concrete structure 2 by each laser radiation pulse and will convert these waves into electric signals which are sent to a signal adjacent analyzer 20, and compared with signals from a reference sensor 21 at the cavity 10.

When laser radiation having a given wavelength range and having a selected energy density pattern, i.e. composed of a given number of pulses at a given pulse rate, with each pulse having a given duration, and a given energy density at the point of impact, impinges on a concrete structure, the quantity of material removed will be a function of the strength and composition of the concrete. As the laser radiation vaporizes a portion of the concrete, spectral analysis of radiation emitted by the vaporized material can provide identification of the concrete composition and then strength can then be determined as a function of the quantity and type of material removed.

When a succession of laser pulses are all directed at the same point on a concrete structure, each pulse vaporizes a small quantity of concrete at a respective depth below the original surface of the structure. Because concrete inherently has a certain heterogeneity, the spectra emitted in response to successive radiation pulses will vary from one another in a pattern which bears a relation to the concrete composition. The sequence of spectra can be used to identify the concrete composition and then the strength of the concrete can be determined from measurement of the volume of concrete removed by the laser pulse sequence.

Prior to testing concrete structures in the field, the spectral patterns of different concrete compositions may be determined in a laboratory environment to produce reference data. For each composition, a plurality of samples having different, independently measured, strengths are each subjected to laser radiation having a defined form during which energy emitted by vaporized concrete is detected and subjected to spectral analysis. The radiation is formed as a beam which is aimed at a fixed point of each sample. After delivery of the laser radiation to each sample, the volume of concrete removed is determined, for example by measuring the depth of the hole or cavity formed by the radiation. It is then possible, for a given composition, to derive a curve of concrete strength vs. cavity depth, the concrete strength being separately determined by any conventional method. Spectral data, acoustic data, concrete strength, and cavity depth data are then stored for each composition.

The rate of removal, or the total quantity of material removed, can be measured in a number of ways. Various techniques and physical principles that will be discussed below are applicable to production of reference data, which was discussed above, and to the production of test data on concrete structures in the field.

For example, the volume of material removed can be detected by visual, remote visual, optical probes such as laser radar or laser interferometers, or mechanical probes and calipers. Alternatively, acoustic shock measurements can be employed on the basis that the intensity of each acoustic report is proportional to the volume of material removed by a laser radiation pulse. Each laser pulse can convert a portion of the target material to a plasma. The expansion and collapse of this plasma is transonic, resulting in an acoustic pulse. The energy of this pulse is related to the volume/mass of material converted to plasma and thus is an indicator of the amount of material removed per pulse. Laboratory environment testing will produce reference data for the cement and a variety of aggregate materials, establishing the correlation between the acoustic pulse volume and the mass of material removed. Accounting for geometry, the time of travel of the acoustic pulse in the concrete (normalized with the first pulse) can be used to determine penetration depth. Also, this time of flight (first pulse) can be used to determine the speed of sound in the concrete. The speed of sound is another parameter of the concrete that may provide an additional correlation with the strength/quality of the concrete being tested. Acoustic pulse intensity and timing can be measured by proper placement of acoustic transducers (piezoelectric for example) on and around the concrete structure and monitoring the transducer signal outputs with a digital storage oscilloscope (for example), for timing/speed of sound measurements, the oscilloscope can be triggered photoelectrically by the laser pulse and the time to receiving an acoustic pulse at a given transducer measured directly on the scope.

According to another possibility, plasma light intensity can be measured, on the basis that the total light emitted from material which has been ablated is proportional to the quantity of material removed.

The spectroscopic determinations will provide an indication of the chemical and physical properties or character of both the cementaceous components and the aggregates in a concrete body.

Then, in the field, laser radiation having the same defined form is directed at a concrete structure to be tested, and the energy emitted by the vaporized concrete is detected and subjected to spectral analysis. The resulting spectral data is compared with the stored data to identify the concrete composition. Based on this identification, the data representing the corresponding concrete strength vs. cavity depth curve is selected. The depth or volume of the cavity formed in the concrete is measured by any suitable method and the measurement is converted to a strength value in accordance with the selected data.

The procedure of delivering laser radiation pulses to a concrete structure and effecting spectral analysis can also be employed to observe the condition of a concrete structure. For example, in a concrete structure containing steel reinforcing bars there is a tendency for the bars to deteriorate with age, particularly if the concrete develops cracks which bring the bars into contact with air and water.

When the steel bars deteriorate, iron diffuses from the bars into the concrete. Therefore, if a hole or cavity is created in a reinforced concrete structure, the spectra generated in response to successive laser radiation pulses will be indicative of the condition of the reinforcing bars. If the bars have not experienced any deterioration, the spectra will not show the presence of iron essentially until the hole or cavity reaches a bar, at which time the spectra will change abruptly to have a predominant iron component. If the reinforcing bars have experienced deterioration, the successive spectra will show a gradually increasing iron presence even if the hole or cavity is being formed at some distance from a bar. The more advanced the deterioration, the more gradual the gradient of iron in the concrete.

As regards the laser radiation, which is preferably in the form of a train of pulses, one wavelength which would prove suitable is 0.532 µm, which can be produced by frequency doubling the fundamental output of an Nd:YAG laser. The radiation employed for a given test will consist of a given number of pulses having a given pulse rate and a given pulse duration, together with a fixed power level and beam diameter at the point where hole 10 is being formed. To the extent possible, the same energy density pattern should be employed for the radiation used to obtain reference curves and the radiation used to test concrete structures in the field.

Thus, according to the invention, laser ablation is employed to remove quantities of concrete, with the quantity of concrete removed by laser radiation having a given form being related to the strength or integrity of the concrete. Meaningful information can be obtained upon removal of a relatively small quantity of concrete, for example a cylindrical volume having a diameter of less than 1 mm and a depth of between 2 and 20 mm. The process of the invention can be employed to test concrete in situ and a succession of pulses can be applied to a given area or can be directed to different locations at the surface of the concrete structure.

Since testing can involve removal of only a small quantity of material, the strength of an overall structure will not be measurably reduced, making the process essentially nondestructive in nature.

In accordance with the invention, a succession of laser radiation pulses can be directed at a single location of a concrete structure in order to drill the concrete to depths of up to several meters. This would permit collection of the data described earlier herein and analysis of concrete characteristics down to a substantial depth below the concrete structure surface. The resulting data will be equivalent to that obtained by taking core samples of a concrete structure and extensive laboratory testing, while at the same time the procedure is virtually nondestructive.

Concrete is typically composed essentially of cement, sand and aggregate. The cement is formed by combining a finely ground solid material or mixture with water. Then to produce a concrete mixture, sand and aggregate are added to the cement mixture. The properties of a concrete body depend, inter alia, on the solid material/sand volume ratio and/or certain characteristics of the aggregate, including the aggregate size and the uniformity of dispersal of the aggregate in the finished concrete body.

According to the invention, sequential spectral analysis of radiation emitted by the concrete can be employed to determine the chemical composition of the solid material component and the solid material/sand ratio of the original cement mixture and the nature of the aggregate.

For determining any concrete property or characteristic on the basis of any energy characteristic disclosed herein, measurements obtained from tests on concrete structures in the field are compared with measurement preliminarily obtained from identical tests performed on reference concrete samples for which the property or characteristic in question is already known or is independently determined by an independent test of known reliability.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A method of testing concrete in a structure in situ, comprising:

directing a succession of pulses of laser radiation at a point on the structure so that each pulse effects removal of a quantity of concrete and transfers energy to the concrete;

detecting a characteristic of energy which has been transferred to the concrete;

determining, separately from said detecting step, the total quantity of concrete removed by the succession of pulses; and calculating a property of the concrete on the basis of the detected energy characteristic and the determined total quantity of concrete removed.

2. A method as defined in claim 1 wherein the laser radiation has an energy density and wavelength selected to transfer energy to the concrete in order to effect vaporization of a portion of the concrete and the step of determining comprises detecting radiation emitted by concrete which is vaporized by the laser radiation and performing spectral analysis on the detected radiation.

3. A method as defined in claim 2 wherein the property calculated in said calculating step is the strength of the concrete.

4. A method as defined in claim 2 wherein the property calculated in said calculating step is the physical state of the concrete.

5. A method as defined in claim 2 wherein the concrete contains cement, sand and aggregate, the cement containing finely ground solid material, the concrete having a solid material/sand volume ratio and one property calculated in said calculation step is the solid material/sand ratio.

6. A method as defined in claim 5 wherein a second property calculated in said calculating step is a characteristic of the aggregate.

7. A method as defined in claim 2 wherein the concrete contains cement, sand and aggregate, the cement containing finely ground solid material which has a chemical composition and one property calculated in said calculation step is the chemical composition of the finely ground solid material.

8. A method as defined in claim 7 wherein a second property calculated in said calculating step is a characteristic of the aggregate.

9. A method as defined in claim 2 wherein the concrete contains aggregate having a given size and dispersed throughout the concrete, and one property calculated in said calculating step is a characteristic of the aggregate.

10. A method as defined in claim 9 wherein the characteristic is the size of the aggregate.

11. A method as defined in claim 9 wherein the characteristic is the uniformity of dispersal of the aggregate throughout the concrete.

12. A method as defined in claim 1 wherein the energy transferred to the concrete has the form of acoustic waves.

13. A method as defined in claim 12 wherein the property is the physical state of the concrete.

* * * * *